(12) United States Patent
Naito

(10) Patent No.: US 7,739,079 B2
(45) Date of Patent: Jun. 15, 2010

(54) INFORMATION PROVIDING SYSTEM AND ANALYZER

(75) Inventor: Takamichi Naito, Kobe (JP)

(73) Assignee: Sysmex Corporation, Kobe (JP)

( * ) Notice: Subject to any disclaimer, the term of this patent is extended or adjusted under 35 U.S.C. 154(b) by 185 days.

(21) Appl. No.: 11/731,030

(22) Filed: Mar. 30, 2007

(65) Prior Publication Data

US 2007/0233303 A1    Oct. 4, 2007

(30) Foreign Application Priority Data

Mar. 30, 2006    (JP)    ............... 2006-094571

(51) Int. Cl.
    *G06F 19/00*    (2006.01)
(52) U.S. Cl. ...................................... 702/189
(58) Field of Classification Search ............... 702/189, 702/187, 66–68, 80; 711/100; 707/3, 4
    See application file for complete search history.

(56) References Cited

U.S. PATENT DOCUMENTS

| | | | |
|---|---|---|---|
| 6,275,150 | B1 | 8/2001 | Mandler et al. |
| 6,937,964 | B2 * | 8/2005 | Okuno et al. ............... 702/187 |
| 7,606,680 | B2 * | 10/2009 | Okuno et al. ............... 702/187 |
| 2002/0048050 | A1 * | 4/2002 | Kanematsu et al. ......... 358/437 |
| 2002/0128728 | A1 * | 9/2002 | Murakami et al. ............ 700/10 |
| 2002/0128801 | A1 | 9/2002 | Okuno et al. |
| 2005/0013736 | A1 | 1/2005 | McKeever |
| 2005/0177345 | A1 * | 8/2005 | Okuno et al. ............... 702/187 |
| 2006/0156141 | A1 * | 7/2006 | Ouchi ........................ 714/742 |
| 2006/0174167 | A1 * | 8/2006 | Ito .............................. 714/48 |

FOREIGN PATENT DOCUMENTS

| | | |
|---|---|---|
| EP | 1107159 A2 | 6/2001 |
| JP | 2002-297796 | * 10/2002 |
| JP | 2004-072573 | * 3/2004 |

OTHER PUBLICATIONS

European Search Report for European Application No. 07006536.2, dated Aug. 27, 2009, 2 pages.

* cited by examiner

*Primary Examiner*—Michael P. Nghiem
*Assistant Examiner*—Cindy H Khuu
(74) *Attorney, Agent, or Firm*—Brinks Hofer Gilson & Lione

(57) ABSTRACT

An information providing system comprises an analyzer and an information server communicatively connected to the analyzer through a network, which stores coping information regarding apparatus abnormalities of the analyzer, and the analyzer obtains the coping information corresponding to the apparatus abnormalities that occur to the analyzer from the information server, and displays this coping information on a display unit.

10 Claims, 16 Drawing Sheets

FIG. 4(a)

| Error code | Apparatus abnormalities | Simple information |
|---|---|---|
| 111025 | Sheath pressure abnormality | 1) Adjustment of sheath pressure is required.   2) Please contact technical support center... |
| 113005 | 0.05 MPa pressure abnormality | 1) Please adjust 0.05 MPa pressure.   2) When 0.05 MPa pressure can not be adjusted... |
| 113022 | 0.22 MPa pressure abnormality | 1) Please adjust 0.22 MPa pressure.   2) Check connection of tube, and loosening of nipple... |
| 119010 | Abnormal pressure drop | 1) Malfunction of compressed air source is considered.   Please contact technical support center. |
| ...... | ......... | ............................ |
| ...... | ......... | ............................ |
| ...... | ......... | ............................ |
| ...... | ......... | ............................ |

FIG. 4(b)

| Logon name | Password | Group |
|---|---|---|
| abc | 123 | User group |
| def | 456 | User group |
| ghi | 789 | User group |
| ... | ... | User group |
| ... | ... | User group |
| jkl | 234 | Service engineer group |
| mno | 567 | Service engineer group |
| pqr | 891 | Service engineer group |
| ... | ... | Service engineer group |
| ... | ... | Service engineer group |
| stu | 345 | Manufacturer group |
| vwx | 678 | Manufacturer group |
| yza | 912 | Manufacturer group |
| ... | ... | Manufacturer group |
| ... | ... | Manufacturer group |

FIG. 4(c)

| Group | Error code | Apparatus abnormalities | Address |
|---|---|---|---|
| User group | 111025 | Sheath pressure abnormality | http://www.sysmex/data/user/111025···· |
| | 113005 | 0.05 MPa pressure abnormality | http://www.sysmex/data/user/113005···· |
| | 113022 | 0.22 MPa pressure abnormality | http://www.sysmex/data/user/113022···· |
| | ··· | ··· | http://www.sysmex/data/user/············ |
| | ··· | ··· | http://www.sysmex/data/user/············ |
| Service engineer group | 111025 | Sheath pressure abnormality | http://www.sysmex/data/se/111025···· |
| | 113005 | 0.05 MPa pressure abnormality | http://www.sysmex/data/se/113005···· |
| | 113022 | 0.22 MPa pressure abnormality | http://www.sysmex/data/se/113022···· |
| | ··· | ··· | http://www.sysmex/data/se/············ |
| | ··· | ··· | http://www.sysmex/data/se/············ |
| Producer group | 111025 | Sheath pressure abnormality | http://www.sysmex/data/fu/111025···· |
| | 113005 | 0.05 MPa pressure abnormality | http://www.sysmex/data/fu/113005···· |
| | 113022 | 0.22 MPa pressure abnormality | http://www.sysmex/data/fu/113022···· |
| | ··· | ··· | http://www.sysmex/data/fu/············ |
| | ··· | ··· | http://www.sysmex/data/fu/············ |

FIG. 6(a)

| Address | Abnormal operation | | Coping information directed to user | | |
|---|---|---|---|---|---|
| | Error code | | Text data | Image data | HTML data |
| http://··· ··· | 111025 | Sheath pressure abnormality | ················· | ······ | ······ |
| http://··· ··· | 113005 | 0.05 MPa pressure abnormality | 1 Ok button of help dialog box is pressed to display state display dialog box.<br>2 Front side cover is opened.<br>3 0.05 MPa adjusting regulator is turned so that 0.05 MPa pressure value of state display dialog box shows 0.05.<br>4 Front side cover is closed.<br>5 Button of closing the state display dialog box is pressed.<br><br>* When reset is impossible, please contact technical support center. | ······ | ······ |
| http://··· ··· | 113022 | 0.22 MPa pressure abnormality | ················· | ······ | ······ |
| http://··· ··· | ······ | ············ | ················· | ······ | ······ |

FIG. 6(b)

| Address | Abnormal operation | | Coping information directed to service person | | |
|---|---|---|---|---|---|
| | Error code | | Text data | Image data | HTML data |
| http://··· ··· | 111025 | Sheath pressure abnormality | ·········· | ······ | ······ |
| http://··· ··· | 113005 | 0.05 MPa pressure abnormality | 1 Confirm operation counter<br>2 Ok button of help dialog box is pressed to display state display dialog box.<br>3 Confirm 0.22 MPa pressure value (confirm initial pressure)<br>4 When the number of operations is XX ten thousands or more, or 0.22 MPa pressure value is XX or less, pump is exchanged.<br>5 Front side cover is opened in case of condition other than 4.<br>6 Regulator is turned so that 0.05 MPa pressure value of state display dialog is set at 0.05.<br>7 Front side cover is closed.<br>8 Button of closing the state display dialog box is pressed.<br><br>1 When not restored, the next procedure is executed.<br>2 Sidewall cover is opened.<br>3 Confirm whether or not deterioration is found in tube and nipple.<br>4 Tube and nipple are exchanged as needed<br>5 Open a state display dialog<br>6 Front side cover is opened.<br>6 0.05 MPa adjusting regulator is turned so that 0.05 MPa pressure value of state display dialog box shows 0.05.<br>7 Front side cover is closed.<br>8 Button of closing the state display dialog box is pressed. | ······ | ······ |
| http://··· ··· | 113022 | 0.22 MPa pressure abnormality | ·········· | ······ | ······ |
| http://··· ··· | ······ | ·············· | ·········· | ······ | ······ |

FIG. 6(c)

| Address | Abnormal operation | | Coping information directed to producer group | | |
|---|---|---|---|---|---|
| | Error code | | Text data | Image data | HTML data |
| http://··· ··· | 111025 | Sheath pressure abnormality | ················· ················· ················· | ······ ······ ······ | ······ ······ ······ |
| http://··· ··· | 113005 | 0.05 MPa pressure abnormality | 1  Sidewall cover is opened.<br>2  Confirm connection of tube and when poor connection is found, it is repaired.<br>3  Ok button of help dialog box is pressed to display state display dialog box.<br>4  Front side cover is opened.<br>5  0.05 MPa adjusting regulator is turned so that 0.05 MPa pressure value of state display dialog box shows 0.05.<br>6  Front side cover is closed.<br>7  Sidewall cover is closed.<br>8  Button of closing the state display dialog box is pressed.<br>* When not restored, it is lined-out. | | |
| http://··· ··· | 113022 | 0.22 MPa pressure abnormality | ················· ················· ················· | ······ ······ ······ | ······ ······ ······ |
| http://··· ··· | ······ | ··············· | ················· ················· ················· | ······ ······ ······ | ······ ······ ······ |

INFORMATION PROVIDING SYSTEM AND ANALYZER

RELATED APPLICATIONS

This application claims priority under 35 U.S.C. §119 to Japanese Patent Application No. JP2006-094571 filed Mar. 30, 2006, the entire content of which is hereby incorporated by reference.

FIELD OF THE INVENTION

The present invention relates to an information providing system for providing coping information regarding an analyzer to an operator and the analyzer.

BACKGROUND

In recent years, in order to manage a hardware of the analyzer, there is proposed a system of transmitting abnormal operation status information of the analyzer and its operation history to a terminal, etc, set at a place away from the analyzer, and performing a remote management of the analyzer (for example, see U.S. Patent Application Publication No. 2002/0128801).

In the aforementioned conventional system, when an abnormality occurs to the analyzer, it is possible that a manager who operates the terminal installed at a place away from the analyzer can recognize that abnormality occurs to the analyzer. However, in order to restore the analyzer to a normal state, the operator who actually operates the analyzer must repair and adjust the analyzer in most cases.

For example, when the operator repairs and adjusts the analyzer, who belongs to an end user such as hospital and clinical laboratory where this analyzer is purchased and used, usually, the operator himself/herself grasps a coping process, performs a coping work, and restores this analyzer to a normal operation state by referring to a manual, etc, contacting a help desk on the phone, and the like. In this case, the operator obtains mainly from the manual the coping information regarding an apparatus such as repair and adjustment of the analyzer. Further, the abnormality sometimes occurs even when a service engineer who belongs a manufacturing company of this analyzer or a manufacturer who is involved in production of this analyzer operate the analyzer. Even in these cases, the coping information is mainly obtained from a dedicated manual in the same way as the end user.

Meanwhile, when the abnormality occurs, some analyzers have a function of displaying simple information, which is a simple coping process responding to this abnormality, on a display screen, etc, of the analyzer. However, in many cases, such a simple coping process cannot respond to the abnormality. In addition, since information of the same content is provided to the operator who has a different attribute (such as an end user, a service engineer, and a manufacturer, etc), it cannot be said that sufficient and useful information can be provided to the operator. When the analyzer is in a state requiring a response to abnormality, etc, the operator of this analyzer can obtain the coping information efficiently and can appropriately cope with the abnormality of this analyzer quickly, without referencing the manual, etc, attached with this analyzer and searching and obtaining required information therefrom, if the coping information, being a detailed coping process for this state, can be displayed on the aforementioned display screen.

Meanwhile, when a detailed coping process is provided to the operator, the following problem is involved depending on the display screen of the analyzer. Namely, as the coping information on the analyzer is made further detailed, the problem involved therein is that necessity for always updating the information to the newest information is generated, and necessity for considering a difference of attributes of the operator who refers to this coping information is generated. For example, required coping information is different among the end user such as hospitals and clinical laboratories, the service engineer who belongs to the manufacturing company of this analyzer, and the manufacturer of the analyzer. Therefore, it is necessary to prepare the coping information of a different content in accordance with the operator who refers to this information, resulting in making its information amount enormous. It is difficult to store such an enormous information amount in the analyzer and always update the information to the newest information.

SUMMARY

The scope of the present invention is defined solely by the appended claims, and is not affected to any degree by the statements within this summary.

A first aspect of the present invention is an information providing system comprising:

an analyzer for analyzing a sample, having a memory which stores first coping information indicating a coping process for the analyzer; and a database apparatus communicatively connected to the analyzer through a network and storing second coping information indicating more detailed coping process than the first coping information, wherein the analyzer comprises:

a display unit;

first obtaining means for obtaining the first coping information from the memory;

first displaying means for displaying the first coping information obtained by the first obtaining means on the display unit;

second obtaining means for obtaining the second coping information from the database apparatus; and second displaying means for displaying the second coping information obtained by the second obtaining means on the display unit.

A second aspect of the present invention is an information providing system comprising:

an analyzer for analyzing a sample; and a coping information database that stores coping information respectively indicating coping processes for each of a plurality of groups previously divided based on predetermined attributes of operators of the analyzer, to cope with status of the analyzer, wherein the analyzer comprises:

a display unit;

obtaining means for obtaining the coping information corresponding to status of the analyzer and a group to which an operator of the analyzer belongs from the coping information database; and coping information displaying means for displaying the coping information obtained by the obtaining means on the display unit.

A third aspect of the present invention is an analyzer for analyzing a sample, comprising:

a display unit;

a memory that stores first coping information indicating a coping process for the analyzer;

first obtaining means for obtaining the first coping information from the memory;

first displaying means for displaying the first coping information obtained by the first obtaining means on the display unit;

second obtaining means for obtaining second coping information indicating a more detailed coping process than the first coping information from a database apparatus that stores the second coping information, communicatively connected to the analyzer through a network; and second displaying means for displaying the second coping information obtained by the second obtaining means on the display unit.

A fourth aspect of the present invention is an analyzer for analyzing a sample comprising:

a display unit;

obtaining means for obtaining coping information corresponding to status of the analyzer and a group to which an operator of the analyzer belongs, from a coping information database that stores the coping information; and coping information displaying means for displaying the coping information obtained by the obtaining means on the display unit.

BRIEF DESCRIPTION OF THE DRAWINGS

FIG. 4(a) is a view showing an example of a simple information database.

FIG. 4(b) is a view showing an example of a group identifying information database.

FIG. 4(c) is a view showing an example of a position information database.

FIG. 6(a) is a view exemplifying a coping information database directed to a user group.

FIG. 6(b) is a view exemplifying a coping information database directed to a service engineer group.

FIG. 6(c) is a view exemplifying the coping information database directed to a manufacturer group.

DETAILED DESCRIPTION OF THE EMBODIMENT

Preferred embodiments of an information providing system and an analyzer of the present invention will be explained based on the drawings hereafter.

Figure 1:
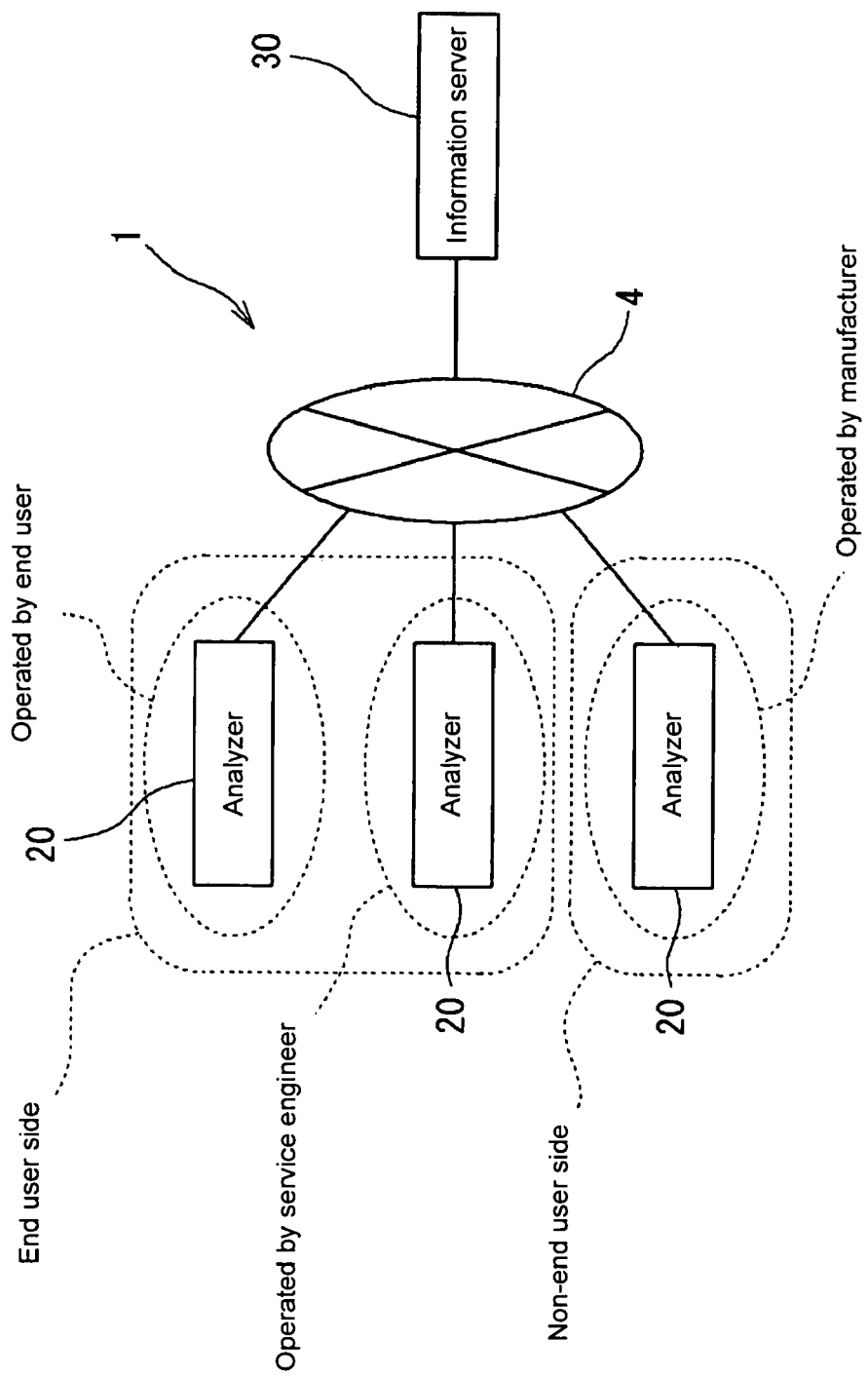
FIG. 1 is a block diagram showing a structure of an entire body of an information providing system directed to a particle analyzer for analyzing cells and bacteria contained in the urine, according to a first embodiment of the present invention.

FIG. 1 is a block diagram showing a structure of an entire body of the information providing system directed to a many item-hemocyte analyzer that performs analysis of blood. In the figure, an information providing system 1 includes a plurality of analyzers 20 and an information server 30 as a database device in which information to be supplied to these analyzers 20 is stored, and they are mutually communicatively connected through a network 4 such as an Internet and a dedicated network. As shown in the figure, the plurality of analyzers 20 are given as examples such as being purchased, possessed, and installed in a facility (end user side) of a hospital and an clinical laboratory, etc, (operated by a service engineer for repairing and adjusting the analyzers 20 possessed by the end user such as stuff of the hospital and the clinical laboratory and the end user), and such as being installed in the facility of a plant, etc, (non-end user side) on the manufacturer side of these analyzers 20 (for example, the manufacturer in the plant operates the analyzer during inspection in a manufacturing intermediate step and assembly work, in a production plant of these analyzers 20).

Figure 2:
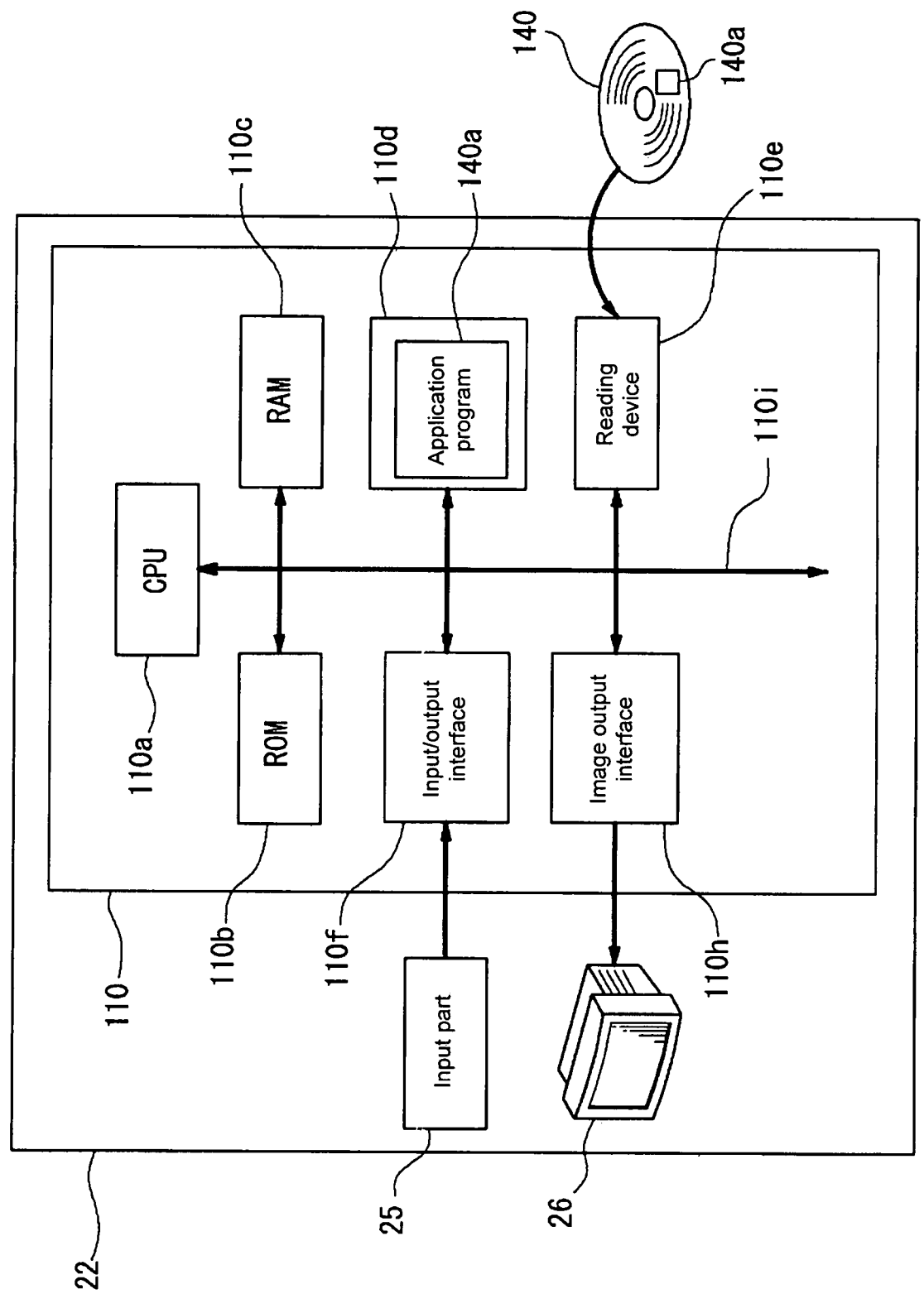
FIG. 2 is a block diagram showing a hardware structure of a controller.

As described later, the analyzer 20 has an analyzer main body for performing a measurement of a sample such as blood, and a controller 22 for controlling this analyzer main body and collecting/analyzing measurement data. FIG. 2 is a block diagram showing a hardware structure of the controller 22. The controller 22 has a computer mainly constituted of a main body 110, a display unit 26, and an input part 25. The main body 110 is mainly constituted of a CPU 110a, a ROM 110b, a RAM 110c, a hard disk 110d, a reading device 110e, an input/output interface 110f, and an image output interface 110h, wherein the CPU 110a, the ROM 110b, the RAM 110c, the hard disk 110d, the reading device 110e, the input/output interface 110f, and the image output interface 110h are connected one another by a bus 110i to attain data communication among them.

The CPU 110a is capable of executing a computer program stored in the ROM 110b and a computer program loaded into the RAM 110c. Then, when this CPU 110a executes an application program, etc, for realizing an operating system or a system of the present invention, each function block, as will be described later, is realized, and the computer functions as the controller 22.

The ROM 110b is constituted of a mask ROM, a PROM, an EPROM, and an EEPROM, etc, and the computer program and data used for this computer program executed by the CPU 110a are recorded therein The RAM 110c is constituted of a SRAM or a DRAM, etc. The RAM 110c is used for reading the computer program recorded in the ROM 110b and the hard disk 110d. In addition, when these computer programs are executed, the RAM 110c is utilized as a working area.

The hard disk 110d has installed therein various computer programs and the data used for executing these computer programs executed by the CPU 110a, such as the operating system and the application program. Each database as will be described later is also stored in this hard disk 110d.

The reading device 110Se is constituted of a flexible disk drive, a CD-ROM drive, or a DVD-ROM drive, etc, and can read the computer program or the data recorded in a portable-type recording medium 140. In addition, the portable-type recording medium 140 stores therein an application program 140a for making the computer function as a system, thus making it possible to make this computer read the application program 140a of the present invention from this portable-type recording medium 140 and install this application program 140a on the hard disk 110d.

Note that the aforementioned application program 140a is not only provided by the portable-type recording medium 140, but also can be provided through an electrical communication line from an external apparatus communicatively connected to the computer by the electrical communication line (regardless of wired or wireless). For example, when the aforementioned application program is stored in the hard disk of a server computer for providing the application program on the Internet, it is possible to access this server computer, download this computer program, and install it on the hard disk 110d.

The input/output interface 110f is constituted of a serial interface such as USB, IEEE1394, RS-232C, a parallel interface such as SCSI, IDE, IEEE1284, and an analogue interface such as a D/A converter and an A/D converter. The input part 25 composed of a keyboard and a mouse, etc, is connected to the input/output interface 110f, and by using this input part 25 by a user, the data can be inputted in the computer.

The image output interface 110h is connected to the display unit 26, being a display constituted of an LCD or a CRT, etc, and outputs to the display unit 26 an image signal in accordance with image data supplied from the CPU 110a. The display unit 26 displays an image (screen), in accordance with the image signal thus inputted.

Figure 3:
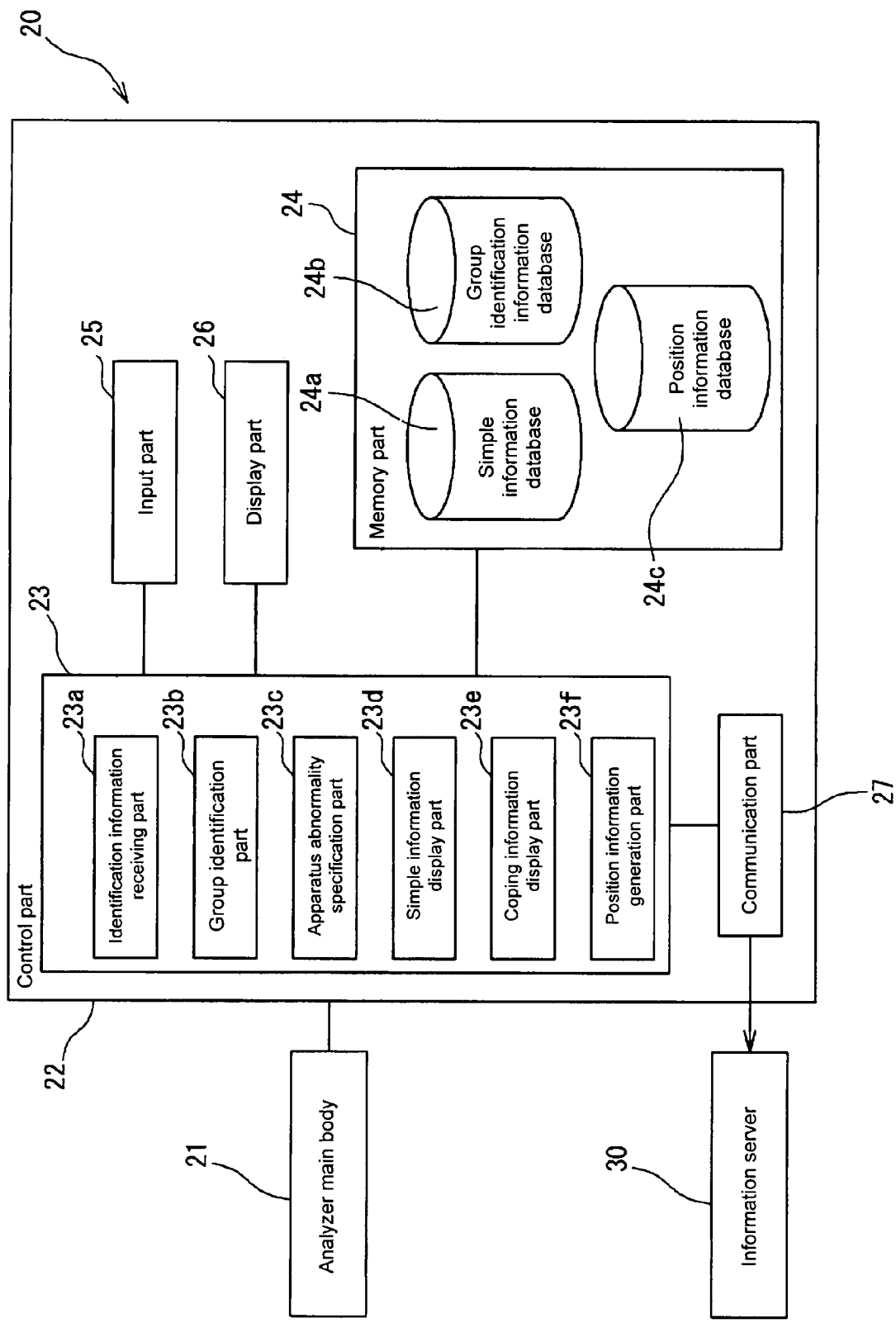
FIG. 3 is a block diagram showing the structure of the analyzer in FIG. 1.

Next, explanation is given to a function of the analyzer 20 having the controller 22 of a hardware structure as described above. FIG. 3 is a block diagram showing the function realized by the analyzer 20. As shown in the figure, the controller 22 having the analyzer main body 21 connected thereto for performing a measurement of a sample such as blood, has a control part 23 for generally controlling the analyzer main body 21 and controlling each part of this controller 22; a memory 24 composed of the aforementioned hard disk 110d and the RAM 110c, etc; and a communication part 27 for performing communication with outside. Also, the input part 25 and the display unit 26 composed of the keyboard and the mouse, etc, as described above are connected to the control part 23.

The communication part 27 is connected to the information server 30 through a network 4 (FIG. 1), to realize the communication between the controller 22 and the information server 30.

The display unit 26 displays various kinds of information such as an analysis result, for the operator who operates this analyzer 20. In addition, the operator can display on the screen of the display unit 26, being the display, an operation part operable by the operator using the input part 25 such as a mouse, etc.

Note that, as described above, the "operator" who operates the analyzer 20 includes the aforementioned end user such as stuff of the hospital and the clinical laboratory, the service engineer who visits to the end user side and performs repair/adjustment work, and the manufacturer who performs inspection and adjustment work in a production plant.

The control part 23 functionally includes an identification information reception part 23a for receiving identification information such as logon name of the operator who operates the analyzer 20; a group identification part 23b for identifying what group, as will be described later, the aforementioned operator belongs to; an apparatus abnormality specification part 23c for detecting and specifying apparatus abnormalities of the analyzer main body 21; a simple information display unit 23d for displaying the simple information indicating a simple coping process corresponding to the abnormalities of the analyzer main body 21; a coping information display unit 23e for obtaining the coping information indicating a detailed coping process corresponding to a specified apparatus abnormality from the information server 30, and displaying it to the operator, in accordance with the request of the operator; and a position information generation part 23f for generating the position information in the information server 30 in which the coping information required for obtaining the coping information from the information server 30 by the coping information display unit 23e.

When the operator starts the analyzer 20, the identification information reception part 23a displays, on the screen of the display unit 26, a dialog box as will be described later for inputting the logon name as the identification information of the operator, and receives the logon name previously allotted to the operator.

The group identification part 23b refers to a group identification information database 24b, as will be described later, stored in the memory 24, and identifies what group, as will be described later, the logon name received by the identification information reception part 23a belongs to.

The apparatus abnormality specification part 23c obtains various kinds of signal information from each kind of sensor, etc, of the analyzer main body 21, and specifies the apparatus abnormality from this signal information.

The coping information display unit 23e has a function as a web browser for displaying information on the screen of the display unit 26, and displays the coping information obtained from the information server 30 in a window of this web browser.

The memory 24 stores a simple information database 24a including the simple information corresponding to each of the various kinds of apparatus abnormalities generated in the analyzer main body 21; a group identification information database 24b referenced for identifying the group of the operator by the group identification part 23b; and a position information database 24c referenced for generating the position information by the position information generation part 23f, in addition to the aforementioned operating system and computer program such as an application program.

For example, as shown in FIG. 4(a), the simple information database 24a is so organized that various kinds of apparatus abnormalities generated in the analyzer main body 21 and the simple information as the coping information corresponding to such apparatus abnormalities are correspondingly stored, and the simple information corresponding to the apparatus abnormality generated in the analyzer main body 21 can be easily obtained.

The group identification information database 24b includes the information used for identifying what group the operator who operates this analyzer 20 belongs to out of a plurality of groups previously divided based on a predetermined attribute. Here, in this embodiment, in accordance with the attribute of the operator, three groups are defined, such as "user group", "service engineer group", and "manufacturer group". The "user group" is the group constituted by the end user who purchases and possesses this analyzer 20 and performs analysis measurement, the "service engineer group" is the group constituted by the service engineer who dedicatedly performs inspection, maintenance, and repair of the analyzer 20, and the "manufacturer group" is the group constituted by the manufacturer such as a person in charge of inspection and a person in charge of manufacture who operate the analyzer 20 in the inspection and assembly work in the manufacturing intermediate step of the analyzer 20.

FIG. 4(b) shows an example of the group identification information database 24b. For example, as shown in FIG. 4(b), the group identification information database 24b includes the information whereby the logon name allotted to each of a plurality of operators is corresponded to each group, and based on the logon name at the time of log on by the operator, it is possible to identify what group this operator belongs to. In addition, the information of a password requested to be inputted when the operator inputs the logon name, for example, is stored in this group identification database 24b.

As shown in FIG. 4(c), the position information database 24c is so organized, for example, that various kinds of apparatus abnormalities generated in the aforementioned each group and the analyzer main body 21, and addresses in the information server 30 as will be described later allotted to the coping information corresponding to the apparatus abnormalities are correspondingly stored, and the address allotted to the coping information corresponding to the apparatus abnormalities generated in the analyzer main body 21 can be easily generated.

Note that in this analyzer 20, the controller 22 can be constituted of a personal computer, etc, and this personal computer can be connected to the analyzer main body 21, or the analyzer main body 21 and the controller 22 may be integrally constituted.

Figure 5:
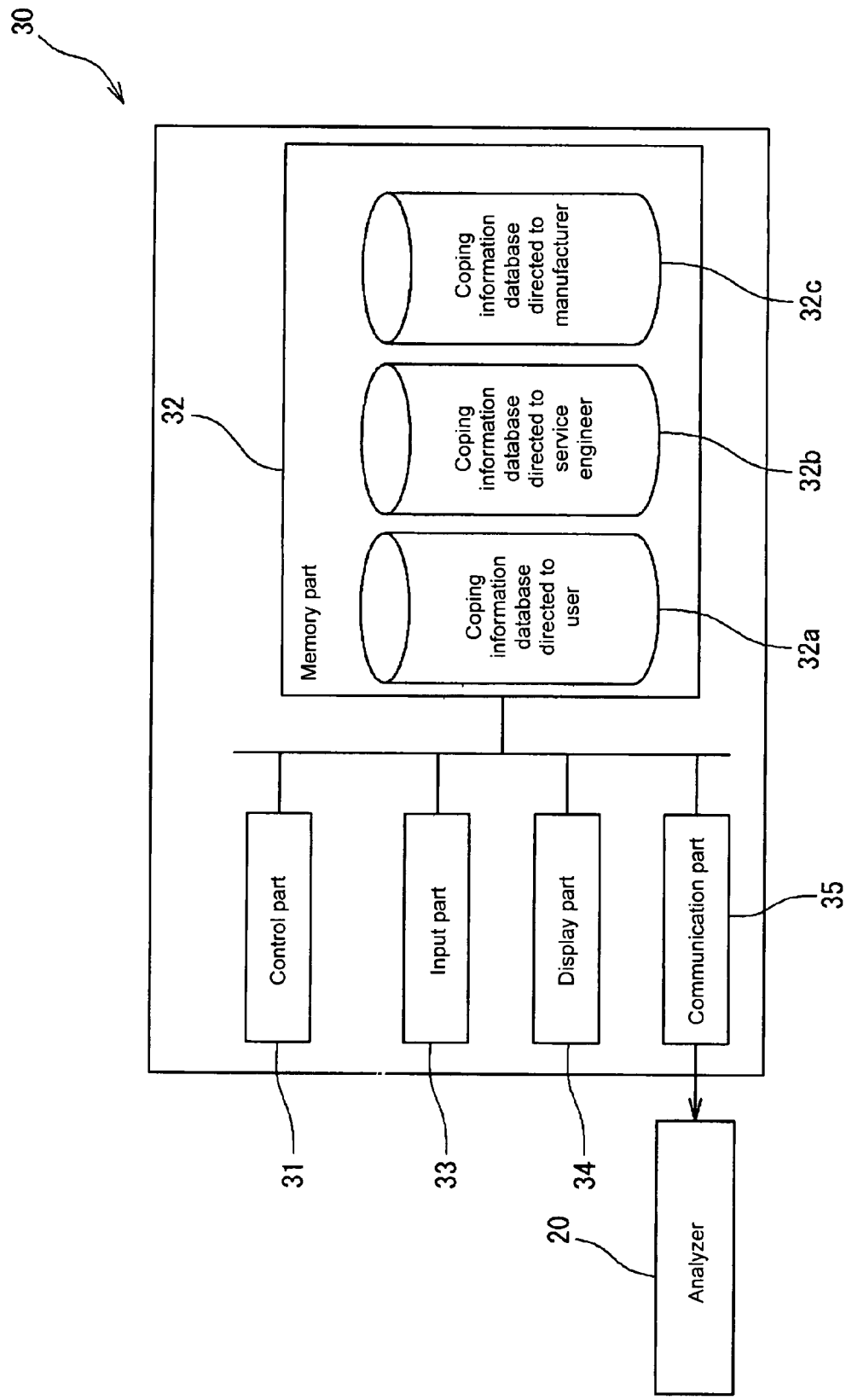
FIG. 5 is a block diagram showing the structure of an information server.

Meanwhile, the information server 30 connected to the analyzer 20 through the network 4 has approximately the same hardware structure as that of the controller 22 as shown in FIG. 2, such as a personal computer and a work station, and has a function as a database server and also has a function as a web server. FIG. 5 is a block diagram showing the structure of the information server 30. As shown in the figure, the information server 30 has a control part 31 for generally controlling each part of the information server 30; a memory 32 composed of a hard disk and a memory, etc; an input part 33 such as keyboard and mouse; a display unit 34 such as a display, etc, and a communication part 35 for performing communication with the analyzer 20.

In accordance with the request from the analyzer 20, the control part 31 selects required information from the coping information databases 32a to 32c corresponding to each group stored in the memory 32, and transmits it to the analyzer 20 through the communication part 35 as the data described in a web data format such as an HTML format.

In addition to the operating system, etc, for operating the information server 30, the memory 32 stores a coping information database 32a directed to a user group; a coping information database 32b directed to a service engineer group; and a coping information database 32c directed to a manufacturer group, wherein the coping information corresponding to various apparatus abnormalities is made into a database. These databases 32a to 32c store group-categorized coping information edited into a content corresponding to the attribute of the aforementioned three groups, by making this coping information into a database for each group.

FIGS. 6(a) to (c) show an example of the aforementioned each coping information databases 32a to 32c stored in the memory 32, FIG. 6(a) shows the coping information database 32a directed to the user group, FIG. 6(b) shows the coping information database 32b directed to the service engineer group, and FIG. 6(c) shows the coping information database 32c directed to the manufacturer group, respectively. As shown in FIGS. 6(a) to (c), in each coping information database, the coping information as the detailed coping information corresponding to the apparatus abnormalities of the analyzer main body 21 is organized and stored. As shown in FIGS. 6(a) to (c), this coping information has text data indicating the coping information, image data for illustrating the coping information to the operator or its link, and HTML data for showing them on the web browser, and when this coping information is transmitted to the analyzer 20, a coping information display unit 23 can display such text data and image data, etc, on the web browser.

In addition, the address as the position information used for showing its storage position is individually allotted to the coping information corresponding to these apparatus abnormalities, and when the analyzer 20 requests the coping information, required information is easily specified based on the address generated by the position information generation part 23f. As shown in the text data of FIGS. 6(a) to (c), the content of the coping information stored in the coping information databases 32a to 32c is edited in accordance with the attribute of the group such as an object and work content of the group and knowledge of a member of the group, and the content different for each group is stored.

Also, in addition to the aforementioned database, the memory 32 may store a similar database in a different analyzer or the analyzer having a different specification even in a case of the same model. In this case, by adding in the aforementioned address, the information on the model of the analyzer and the information used for classifying its specification, etc, the coping information according to the individual case can be stored even in a different analyzer and the analyzer having different specification although having the same model, and the information can be provided.

Note that the information server 30 is not required to be constituted of one set of personal computer, but may be constituted of a plurality of sets of computer apparatuses.

With the above-described structure, the information server 30 receives the access from the analyzer 20 as a web server through the network 4, and provides the coping information stored in the coping information databases 32a to 32c, to the analyzer 20, being an access source, as the HTML data. Note that if the data that can be displayed by the web browser, the data is not limited to the HTML data, and other data such as JAVA (registered trademark) and JavaScript (registered trademark) or the data obtained by combining them may be generated and provided to the analyzer 20.

Figure 7:
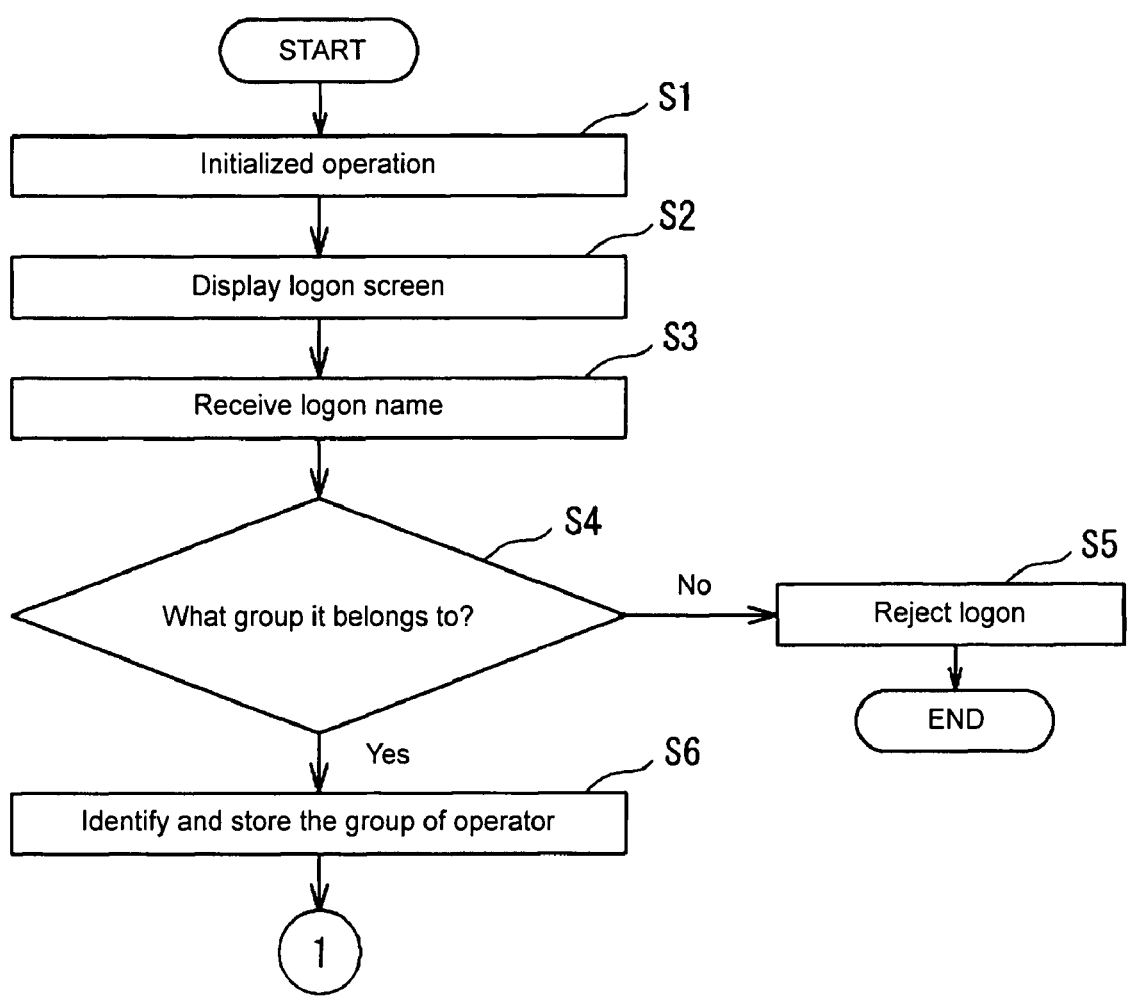
FIG. 7 is a flowchart showing an operation of an information providing system from activating the analyzer until a measurement of a sample becomes possible.

Next, regarding the operation of the information providing system 1 having the above-described structure, explanation will be given to a procedure for executing analysis by using the analyzer 20 by the operator. FIG. 7 is a flowchart showing the operation of the information providing system 1 from the time point when the operator who operates the analyzer 20 starts this analyzer 20 to the time point when the measurement of the sample is possible.

Figure 8:
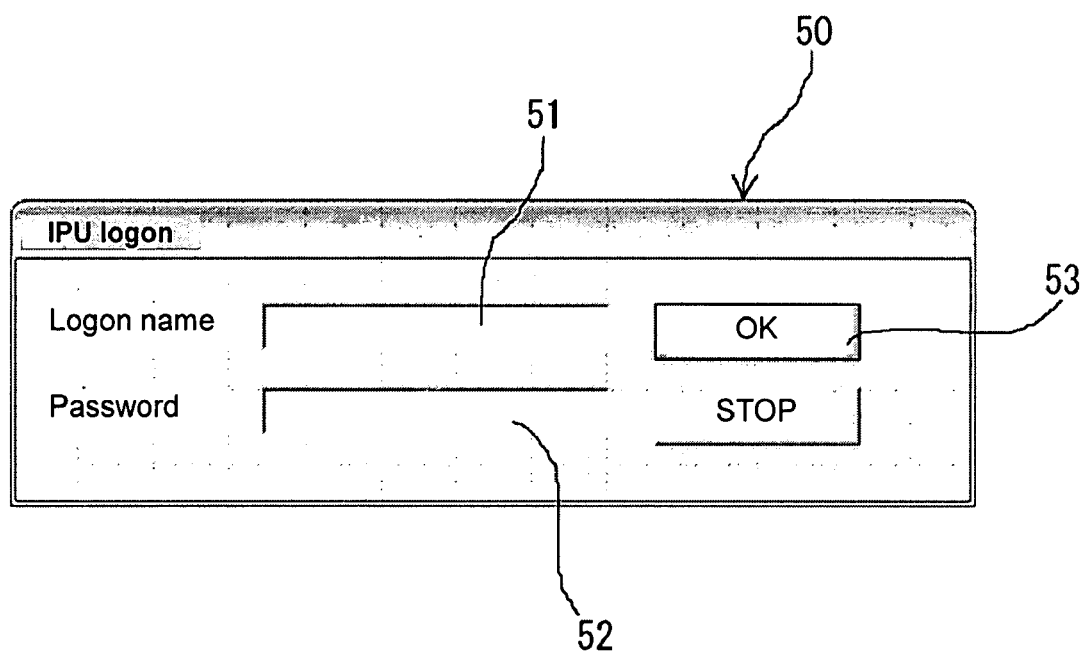
FIG. 8 is a view showing an example of a dialogue box for requiring log on, displayed on a display unit.

In the figure, when the operator starts the analyzer 20 first, the identification information reception part 23a of the control part 23 of the analyzer 20 displays the dialog box to log on to the operation system and the information providing system on the display unit 34, and requests the operator to log on thereto (step S1). FIG. 8 is a view showing an example of the dialog box for requesting the operator to log on, displayed on the display unit 34. The dialog box 50 in the figure has a logon name input part 51 for inputting the logon name previously allotted to each operator, and a password input part 52 for inputting the password corresponding to the logon name input part 51. The operator inputs the logon name and the password allotted to himself/herself by the keyboard, etc, constituting the input part 33, and clicks a button 53 in the dialog box 50. When the button 53 is clicked, the identification information reception part 23a receives the logon name and the password inputted in the dialog box 50 (step S2).

In FIG. 7 again, when the identification information reception part 23a receives the logon name and the password, the group identification part 23b determines what group of the aforementioned three groups, the logon name received by the identification information reception part 23a belongs to (step S3). The group identification part 23b refers to the group identification information database 24b (FIG. 3), and rejects log on when the inputted logon name belongs to none of the groups, or when the password does not match (step S4). Therefore, it is possible to exclude a person who does not know the logon name registered in the group identification information database 24b, from logging on. This contributes to preventing an external person from using this analyzer 20 and the information providing system 1.

When the inputted logon name is determined to belong to any one of the aforementioned three groups, the group identification part 23b identifies what group the logon name belongs to, out of the aforementioned three groups, and stores in the memory 24 a group name consequently identified and the inputted logon name (step S5). As described above, the analyzer 20 can grasp whether or not the present operator belongs to any one of the groups. In step S5, when the identified group name and the inputted logon name are stored, the operator can give an instruction to perform an analysis operation of the analyzer 20.

Figure 9:
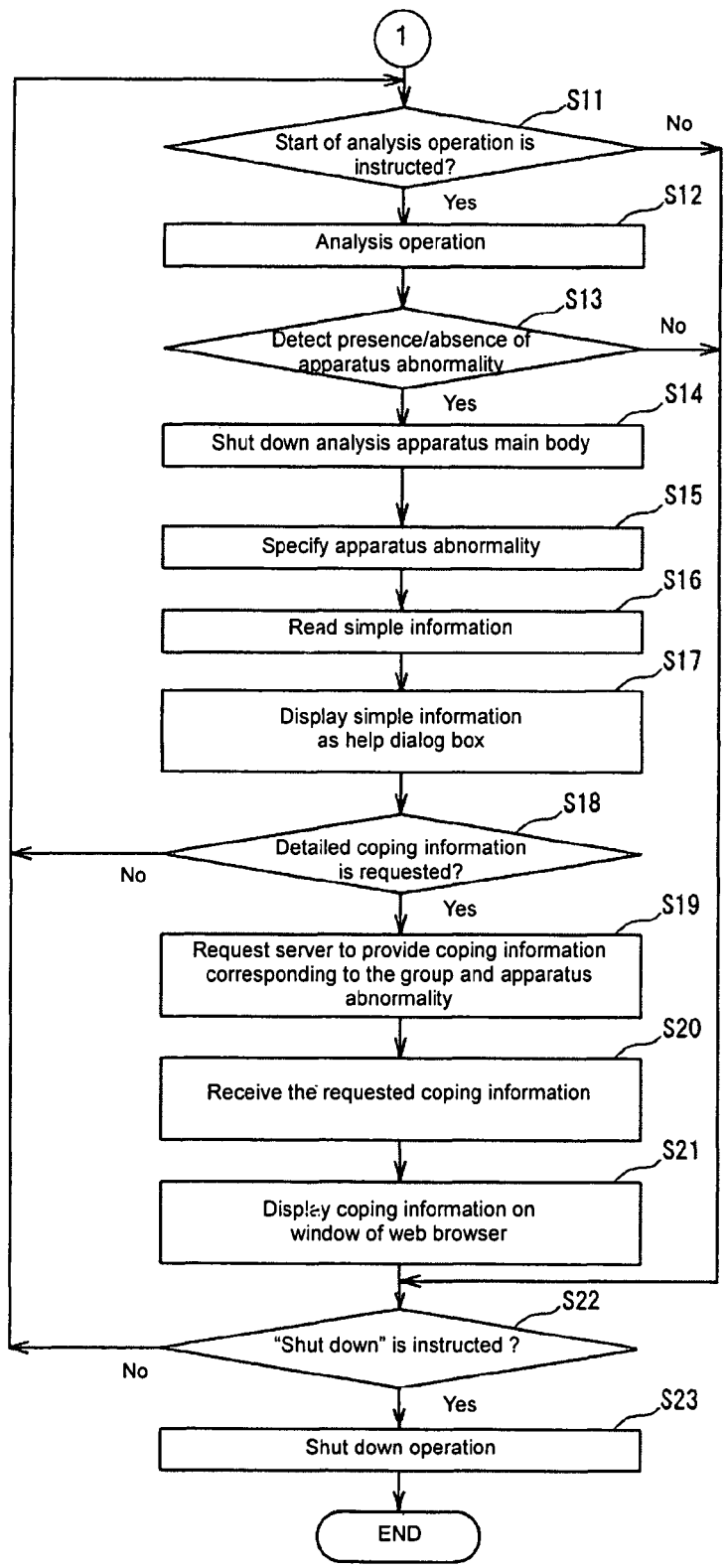
FIG. 9 is a flowchart showing the operation of the information providing system when an analysis operation is executed.

Next, the analysis operation of the information analysis system according to this embodiment will be explained. FIG. 9 is a flowchart showing the operation of the information providing system, when the apparatus abnormalities are generated during analysis operation of the analyzer 20. In the figure, as described above, when the logon by the operator is successful, the analysis operation is executed by performing a predetermined operation by the operator. The control part 23 determines whether or not the instruction to start analysis operation is received from the operator (step S11), and when so instructed, executes the analysis operation (step S12). When the apparatus abnormalities are generated during the analysis operation, the apparatus abnormality specification part 23c detects the apparatus abnormalities (step S13). When the apparatus abnormality specification part 23c does not detect the apparatus abnormalities, the analysis operation is maintained. Meanwhile, when the apparatus abnormality specification part 23c detects the apparatus abnormalities generated in the analyzer main body 21, the apparatus abnormality specification part 23c shuts down the analyzer main body 21 (step S14), and specifies what kind of apparatus abnormalities are generated in the analyzer main body 21 (step S15). In addition, the apparatus abnormality specification part 23c obtains various kinds of signal information from each kind of sensor, etc, of the analyzer main body 21, and specifies the apparatus abnormalities from this signal information. For example, the apparatus abnormality specification part 23c receives a pressure value measured by a pressure sensor incorporated into the analyzer main body 21 as the signal information, and when this pressure value becomes lower than a predetermined threshold value, the apparatus abnormality specification part 23c determines it to be the apparatus abnormality. Further, the apparatus abnormality specification part 23c specifies a part becoming a cause of lowering the pressure measured by this pressure sensor, and specifies the apparatus abnormalities. As described above, the apparatus abnormality specification part 23c specifies the apparatus abnormalities that generate in the analyzer main body 21.

Figure 10:
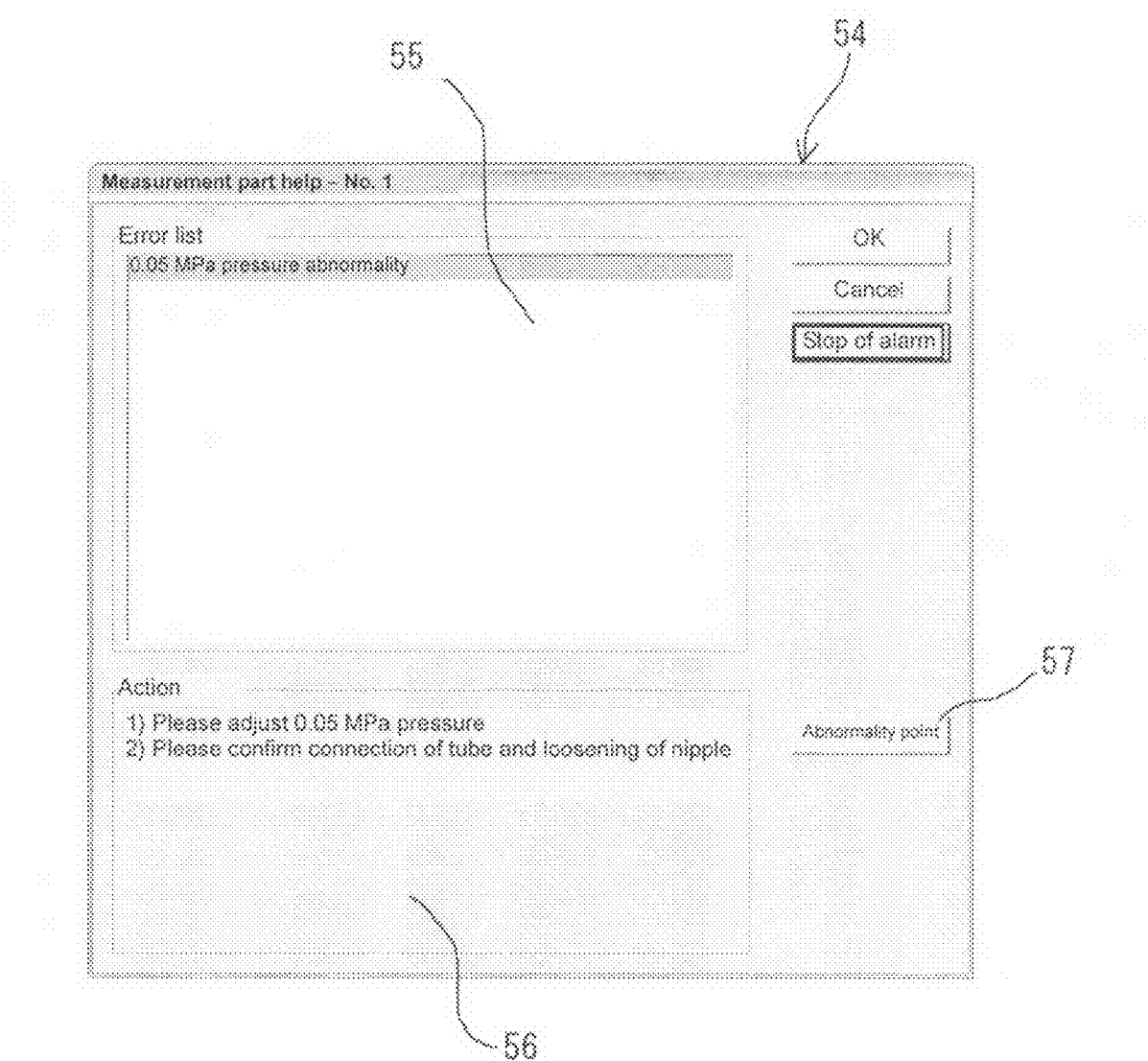
FIG. 10 is a view showing an example of a help dialogue box.

When the apparatus abnormality specification part 23c specifies the apparatus abnormalities, the simple information display unit 23d reads the simple information regarding the apparatus abnormalities thus specified from the simple information database 24a (step S16), and displays a help dialog box showing the read simple information on the screen of the display unit 26 (step S17). FIG. 10 is a view showing an example of the help dialog box shown in step S17. In the figure, the help dialog box 54 as a coping information display screen has an error display unit 55 for showing the apparatus abnormalities specified by the apparatus abnormality specification part 23c and a simple information display unit 56 for showing the simple information corresponding to the apparatus abnormalities displayed on this error display unit 55. When the help dialog box 54 is displayed, the simple information display unit 23d refers to the simple information database 24a stored in the memory 24, and obtains the simple information indicating a simple coping process corresponding to the specified apparatus abnormalities. Then, the obtained simple information is displayed on the simple information display unit 56. Note that this help dialog box 54 can be displayed by operating the help dialog box display unit not shown, displayed on the screen of the display unit 26, and for example, can be arbitrarily displayed when the operator is the service engineer and the manufacturer.

The help dialog box 54 has a detailed information request button 57 for requesting more detailed coping information corresponding to the specified apparatus abnormalities. The detailed information request button 57 displayed in the help dialog box 54 can be operated by the operator using the input part 25 such as a mouse, etc. The control part 23 selects the detailed information request button 57, namely, determines whether or not the request of the more detailed coping information is received (step S18).

When the apparatus abnormalities are coped with by only the simple information displayed in the help dialog box 54, the operator copes with the apparatus abnormalities based on the simple information displayed in the help dialog box 54, without operating the detailed information request button 57. When such a coping process is completed, the processing is returned to step S11, and the instruction of analysis operation can be given again. Here, when the instruction of analysis operation is given, the controller 23 starts the analysis operation again (step S12), and in step S13, detects presence/absence of the apparatus abnormalities, and when the aforementioned specified apparatus abnormalities are solved, continues the analysis operation (step S12). When the apparatus abnormalities are not solved, the controller 23 shuts down the analyzer main body (step S14), specifies the apparatus abnormalities (step S15), and displays the help dialog box 54 again (steps S16 and S17).

Meanwhile, in step S18, when the operator operates the detailed information request button 57 (when the operator requests more detailed coping information), the coping information display unit 23e requests the information server 30 to provide the detailed coping information (step S19). In the coping information databases 32a to 32c stored in the information server 30, as shown in FIGS. 6(a) to (c), a predetermined address is allotted to each coping information corresponding to the apparatus abnormalities. First, the position information generation part 23f generates the address allotted to the coping information corresponding to the specified apparatus abnormalities and a group name (group name identified by the logon name), to which the operator belongs, stored in the memory 24 in step S6 (FIG. 7). The coping information display unit 23e requests the information server 30 to transmit the coping information corresponding to the address generated as described above, based on the address generated by the position information generation part 23f.

When a transmission request of the coping information from the analyzer 20 is received, the controller 31 of the information server 30 obtains the coping information allotted to the aforementioned address from each of the coping information databases 32a to 32c stored in the memory 32, transmits it to the analyzer 20 as the Web data, and the analyzer 20 receives this Web data (step S18). In this way, in this embodiment, the analyzer 20 identifies and grasps the group to which the operator belongs, and therefore, for example, even if a plurality of analyzers 20 access the information server 30, the information server 30 is not required to perform identification of the operator of each of the analyzers thus accessed, thereby reducing its load. In addition, in this embodiment, the analyzer 20 specifies the address in the information server 30 in which required information is stored, and accesses the information server 30. Therefore, the information serve 30 is not required to perform a complicated processing to the request particularly from the analyzer 20, thereby further reducing its load. Note that in this embodiment, the analyzer 20 identifies the group to which the operator belongs. However, it can be so constituted that the analyzer 20 transmits the information used for identifying the group such as a logon name, etc, to the information server 30, and the group, to which the operator belongs, can be identified on the side of the information server 30.

Figure 11:
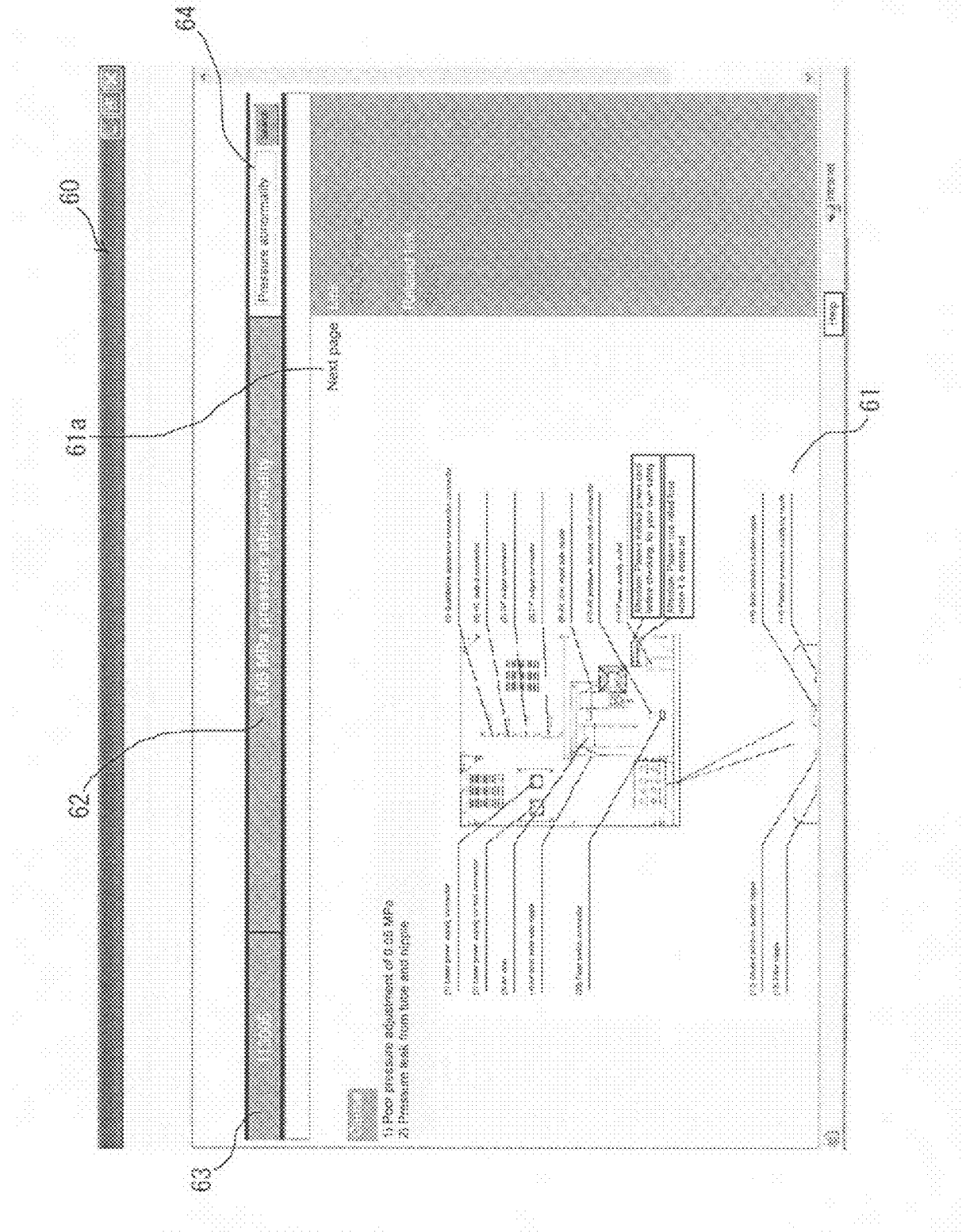
FIG. 11 is a view showing an example of a window of a web browser displayed on the display unit.
Figure 12:
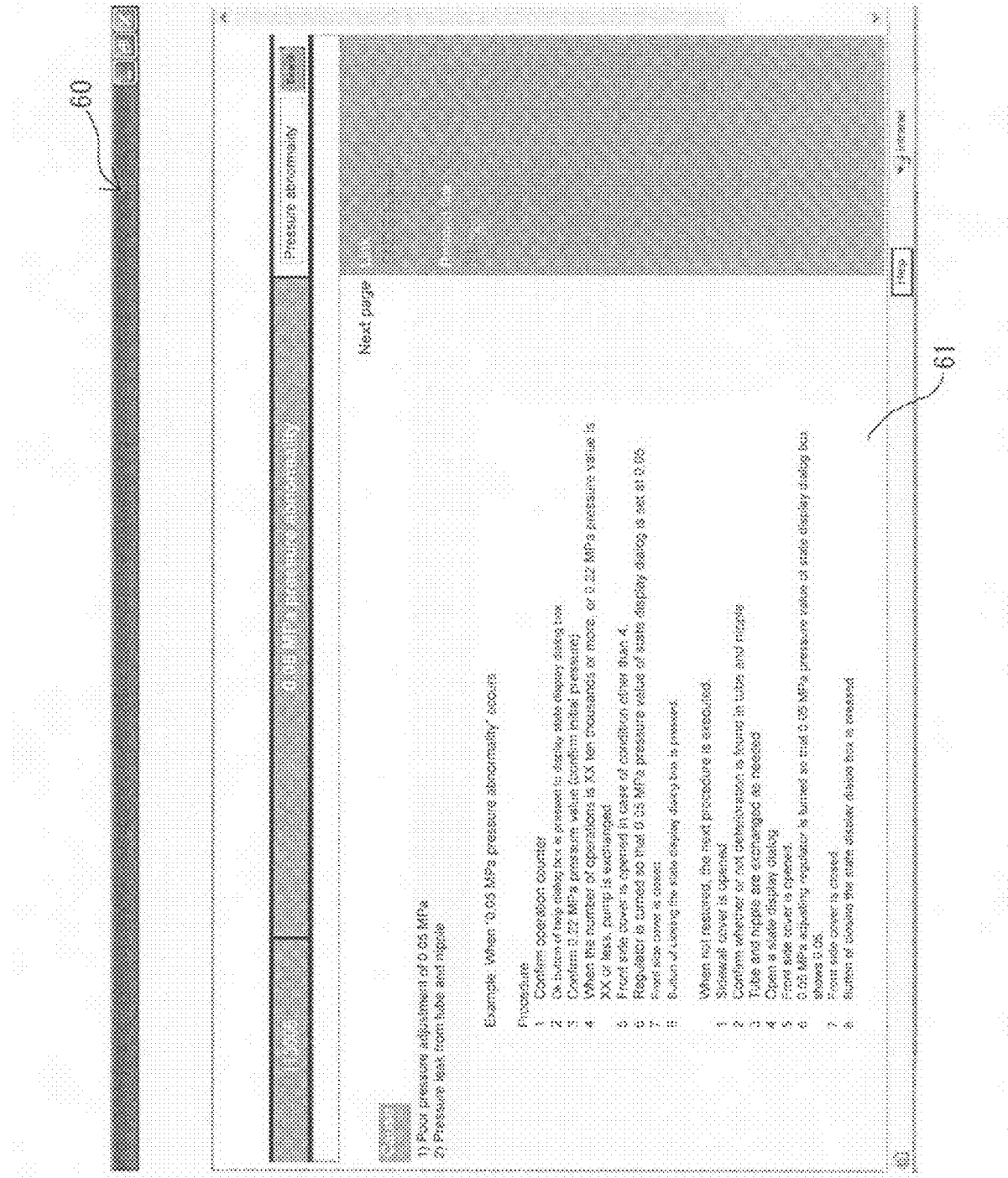
FIG. 12 is a view showing other example of the window of a web browser displayed on the display unit.

The coping information display unit 23e of the analyzer 20 that receives and obtains the coping information from the information server 30 starts the web browser and displays the window of the web browser on the screen of the display unit 26. Then, it displays the coping information obtained from the information server 30, in the window of the web browser (step S21). FIG. 11 and FIG. 12 are views each showing an example of the window of the web browser displayed on the display unit 26. In FIG. 11, the detailed coping information display window 60 has an information display unit 61 for displaying the coping information from the information server 30; an error display unit 62 for showing the apparatus abnormalities which is the subject of the coping information as shown in the information display unit 61; and an error code display unit 63 for showing error codes allotted to the apparatus abnormalities. This information display unit 61 displays a view (FIG. 11) for explaining an adjustment part, etc, of the analyzer main body 21 related to the apparatus abnormalities as the image data included in the coping information obtained from the coping information databases 32a to 32c stored in the memory 32 of the information server 30, and a text of the detailed coping process which must be specifically performed to the apparatus abnormalities. At this time, since the information display unit 61 shows the coping information corresponding to the group to which the operator belongs, the operator can cope with the apparatus abnormalities correspondingly to each attribute. Also, in this embodiment, as described above, since the coping information corresponding to the group identified by the group identification part 23b, to which the operator belongs, can be displayed to the operator, the coping information matching the operator can be provided.

Figure 13:
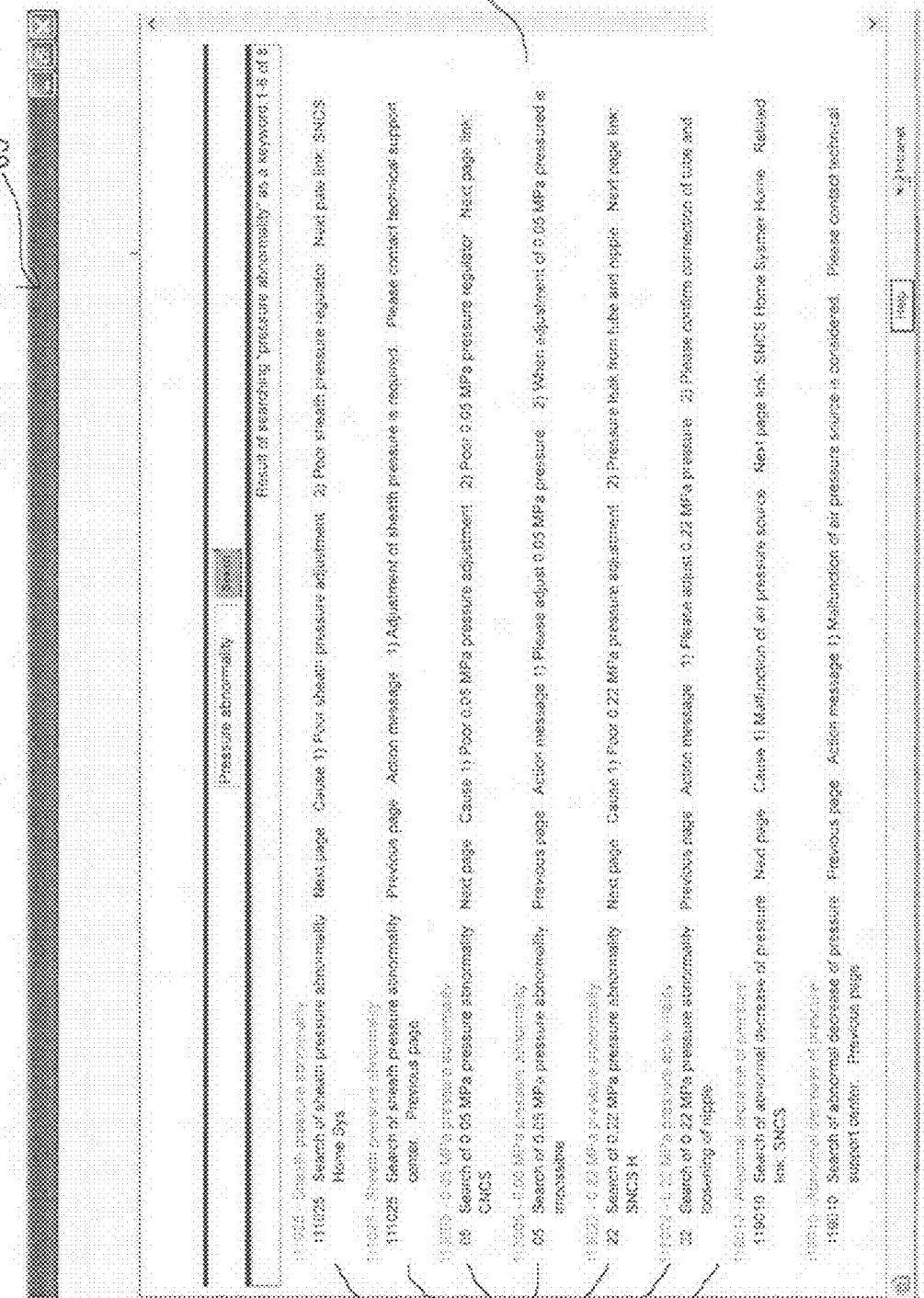
FIG. 13 shows an example of the window of a browser when a key word is inputted in a search keyword input part on the window and showing a search result.

In addition, as shown in FIG. 11, a search keyword input part 64 for searching in the coping information displayed on the information display unit 61 is provided in the window 60, and required information can be easily extracted from the coping information obtained from the information server 30. FIG. 13 shows an example of the window of the browser when a keyword is inputted in the search keyword input part 64 and a search result is shown. A window 65 in FIG. 13 shows a result of searching "pressure abnormality" as a keyword, and shows the information including this "pressure abnormality" on a search result display unit 66. Each search information 66a shown on this search result display unit 66 is linked with a position wherein each search information 66a is described, in an entire body of the coping information obtained from the information server 30, and by clicking each search information 66a, the coping information of the link is shown, thus making it easy to refer to the coping information.

In this way, according to this embodiment, the coping information from the information server 30 is displayed to the operator by the web browser on the display unit 26 as a display screen. Therefore, the coping information can be easily browsed and displayed. In addition, the link with other information can be easily set. This contributes to easy usability in obtaining more information.

In FIG. 9 again, by browsing the content of the window 60 (FIG. 11 and FIG. 12), the operator can grasp the coping process performed to the apparatus abnormalities. Then, the operator copes with the apparatus abnormalities by adjusting/repairing the analyzer main body 21 based on this coping process. When the coping process is completed, the processing is returned to step S11, and the instruction can be given to perform the analysis operation again. Here, when the instruction of the analysis operation is given, the controller 23 starts the analysis operation again (step S12), and in step S13, detects the presence/absence of the apparatus abnormalities, and when the aforementioned specified apparatus abnormalities are solved, continues the analysis operation (step S12). When the apparatus abnormalities are not solved, the control part 23 shuts down the analyzer main body (step S14), specifies the apparatus abnormalities (step S15), and displays the help dialog box 54 again (steps S16 and S17).

Meanwhile, when the instruction to start the analysis operation is not given, the controller 23 determines whether or not the instruction of shutdown by the operator is received (step S22). Then, when the instruction of shutdown is not received, the processing is returned to step S11, and receives the instruction to start the analysis operation again. When the instruction of shutdown is received, a shutdown operation is executed (step S23), and the processing is finished.

Note that in the above-described embodiment, for the simplification of the explanation, it is so explained that the coping information is the information for coping with the abnormalities of the analyzer. However, the present invention is not limited to the apparatus abnormalities as far as the state needs to be coped with, and the information for coping with the adjustment/inspection at the time of producing the analyzer is also included. In this case, when manufacture/adjustment, assembly/adjustment, or inspection of the apparatus is required, such a state is detected, and the coping information indicating a specific work procedure, etc, is provided to the analyzer from the information server.

According to the information providing system of this embodiment thus constituted, it is communicatively connected to the analyzer 20, and is provided with the information server 30 in which the coping information is stored. Therefore, the coping information of enormous information amount is not required to be stored in the analyzer 20. In addition, even when the coping information is provided to a plurality of operators or a plurality of analyzers 20, the coping information can be centrally managed, thereby improving convenience. In addition, by always setting the coping information of the information server 30 in a newest state, newest coping information can be provided to the operator. Further, since the coping information corresponding to the abnormality that generates in the analyzer 20 is displayed, the operator is not required to search and obtain the required information from the manual, etc, thus improving the convenience.

As described above, according to the information providing system 1 of the present invention, the convenience is improved for both of the side providing the coping information and the side referencing the coping information, and the newest coping information can be efficiently provided to the operator. In addition, the coping information provided to the analyzer 20 is centrally managed by the information server 30, and therefore an increase of a management cost can be suppressed.

Further, when the apparatus abnormalities are generated in the analyzer 20, the information providing system of the above-described embodiment displays to the operator the simple information indicating a simple coping process, before detailed coping information is displayed. Therefore, the operator is urged to cope with the apparatus abnormalities based on the simple information first. Then, if the repair/adjustment can be made by the response based on the simple information, the analyzer 20 can be restored more quickly.

In addition, in the analyzer 20 thus constituted also, the newest and useful coping information can be efficiently provided to the operator, as described above.

Note that the information providing system of the present invention is not limited to the above-described embodiment. For example, in the above-described embodiment, the case of using the hemocyte analyzer is exemplified. However, the information providing system of the present invention can be similarly applied to other analyzer. In addition, in the above-described embodiment, the group, to which the operator belongs, is divided into three groups such as "a user", "a service engineer", and "a manufacturer". However, the group can be further subdivided and can be divided into larger numbers of groups. Further, in the above-described embodiment, the data of a web format is provided to the analyzer from the information server, and the coping information is displayed by the web browser. However, the present invention is not limited thereto, and it may be so constituted that a dedicated server program for providing the coping information is installed on the information server and also a dedicated browser program for displaying the coping information is installed on the analyzer, thus providing the information to the analyzer from the information server by a dedicated data format.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. An information providing system comprising:
   an analyzer for analyzing a biological sample comprising a display unit, a controller and a memory configured for storing first coping information indicating a coping process for the analyzer; and
   a database apparatus communicatively connected to the analyzer through a network and storing second coping information indicating more detailed coping process than the first coping information,
   wherein the controller configured for performing first operations comprising:
      detecting abnormality generated in the analyzer,
      obtaining the first coping information regarding the detected abnormality from the memory, and
      displaying the obtained first coping information on the display unit,
   wherein the controller configured for performing second operations comprising:
      receiving a request of displaying a second coping information,
      obtaining the second coping information regarding the detected abnormality from the database apparatus; and
      displaying the obtained second coping information on the display unit.

2. The information providing system according to claim 1, wherein
   the database apparatus stores a plurality of the second coping information individually corresponding to a plurality of groups previously divided based on predetermined attributes of operators of the analyzer, and
   the second coping information obtaining operation is performed by obtaining the second coping information corresponding to a group to which an operator of the analyzer belongs.

3. The information providing system according to claim 2, wherein
   the controller further performs operations comprising:
      receiving identification information used for identifying the group to which the operator belongs; and
      identifying what group of the plurality of groups, the operator belongs to, based on the received identification information,
   wherein the controller performs the second coping information obtaining operation by obtaining the second coping information corresponding to the identified group, to which the operator belongs, from the database apparatus.

4. The information providing system according to claim 2, wherein
   the second coping information is respectively stored in storage positions in the database apparatus corresponding to status of the analyzer and the plurality of groups;
   the second operations further comprises specifying position information indicating a storage position that stores the second coping information corresponding to status of the analyzer and the group to which the operator of the analyzer belongs; and
   the second coping information obtaining operation is performed by obtaining the second coping information based on the specified position information from the database apparatus.

5. The information providing system according to claim 1, wherein
   the first coping information displaying operation is performed by displaying a first screen including the first coping information and a second coping information request operation part on the display unit;
   the request receiving operation is performed by receiving an operation of the second coping information request operation part displayed on the display unit; and
   the second coping information displaying operation is performed by displaying a second screen including the second coping information on the display unit.

6. An analyzer for analyzing a biological sample, comprising:
   a display unit;
   a memory that stores first coping information indicating a coping process for the analyzer to analyze the biological sample; and
   a controller,
   wherein the controller configured for performing first operations comprising: detecting abnormality generated in the analyzer, obtaining the first coping information regarding the detected abnormality from the memory, and displaying the obtained first coping information on the display unit, wherein the controller configured for performing second operations comprising: receiving a request of displaying a second coping information, obtaining second coping information regarding the detected abnormality and indicating a more detailed coping process than the first coping information from a database apparatus that stores a plurality of second coping information, communicatively connected to the analyzer through a network; and displaying the obtained second coping information on the display unit.

7. The analyzer according to claim 6, wherein the database apparatus stores a plurality of the second coping information individually corresponding to a plurality of groups previously divided based on predetermined attributes of operators of the analyzer; and the second coping information obtaining operation is performed by obtaining the second coping information corresponding to a group to which an operator of the analyzer belongs.

8. The analyzer according to claim 7, wherein the controller further performs operations comprising:

receiving identification information used for identifying the group to which the operator belongs; and identifying what group of the plurality of groups the operator belongs to, based on the received identification information, wherein the controller performs the second coping information obtaining operation by obtaining the second coping information corresponding to the identified group, to which the operator belongs, from the database apparatus.

9. The analyzer according to claim 7, wherein the second coping information is respectively stored in storage positions in the database apparatus corresponding to status of the analyzer and the plurality of groups;

the second operations further comprises specifying position information indicating the storage position that stores the second coping information corresponding to the status of the analyzer and the group to which the operator of the analyzer belongs; and the second coping information obtaining operation is performed by obtaining the second coping information based on the specified position information from the database apparatus.

10. The analyzer according to claim 6, wherein the first coping information displaying operation is performed by displaying a first screen including the first coping information and a second coping information request operation part on the display unit;

the request receiving operation is performed by receiving the operation of the second coping information request operation part displayed on the display unit; and the second coping information displaying operation is performed by displaying a second screen including the second coping information on the display unit.

* * * * *